US010441743B1

(12) United States Patent
McKamy (10) Patent No.: US 10,441,743 B1
(45) Date of Patent: Oct. 15, 2019

(54) VIBRATING INFANT GARMENT

(71) Applicant: Collin Michael McKamy, Canyon Lake, TX (US)

(72) Inventor: Collin Michael McKamy, Canyon Lake, TX (US)

(*) Notice: Subject to any disclaimer, the term of this patent is extended or adjusted under 35 U.S.C. 154(b) by 306 days.

(21) Appl. No.: 15/594,639

(22) Filed: May 14, 2017

Related U.S. Application Data

(63) Continuation-in-part of application No. 15/135,077, filed on Apr. 21, 2016, now abandoned.
(60) Provisional application No. 62/151,287, filed on Apr. 22, 2015.

(51) Int. Cl.
*A61M 21/00* (2006.01)
*A61M 21/02* (2006.01)
*A41B 13/00* (2006.01)

(52) U.S. Cl.
CPC .......... *A61M 21/02* (2013.01); *A41B 13/005* (2013.01); *A41B 2400/322* (2013.01); *A61M 2021/0022* (2013.01)

(58) Field of Classification Search
CPC .... A61M 21/02; A61N 5/0618; A61N 5/0621
USPC ..................................... 600/27, 28
See application file for complete search history.

(56) References Cited

U.S. PATENT DOCUMENTS

| 3,310,050 | A | 3/1967 | Goldfarb |
| 3,878,838 | A * | 4/1975 | Lunn .................. A61H 23/00 601/71 |
| 4,124,022 | A | 11/1978 | Gross |
| 4,947,832 | A | 8/1990 | Blitzer |
| 5,660,597 | A | 8/1997 | Fox et al. |
| 6,142,963 | A | 11/2000 | Black et al. |
| 6,175,981 | B1 | 1/2001 | Navarro et al. |
| 6,676,614 | B1 | 1/2004 | Hansen et al. |
| 2002/0065477 | A1 * | 5/2002 | Boyd ................ A61H 19/44 601/47 |
| 2002/0095103 | A1 | 7/2002 | Blue |
| 2005/0183722 | A1 | 8/2005 | Bilgi |
| 2014/0275742 | A1 * | 9/2014 | Andrew ............. A61M 21/02 600/28 |

FOREIGN PATENT DOCUMENTS

EP  1748711 B1  1/2008

* cited by examiner

*Primary Examiner* — Samuel G Gilbert
(74) *Attorney, Agent, or Firm* — Law Office of Sam Sokhansanj PLLC (57) ABSTRACT

An infant garment is disclosed that can provide certain vibrations, in an evenly distributed manner, that can mimic patting and massaging of the infant, thereby providing a calming effect to the infant and promote relaxation and sleep and further prevent irritability, fussing, crying, and screaming, among other advantages. In particular, the infant garment can include a first compartment disposed in a middle region of the garment, wherein the compartment can also include a first flap and a second flap, and wherein the first flap at least partially overlaps the second flap. In addition, the infant garment may also include a second compartment disposed within the first compartment, wherein the second compartment is elastic. Further, the infant garment may also include a vibrating electronic device disposed within the elastic second compartment and secured therein.

18 Claims, 6 Drawing Sheets

VIBRATING INFANT GARMENT

CROSS REFERENCE TO RELATED APPLICATIONS

This application is continuation-in-part (CIP) of U.S. Non-Provisional Application No. 15/135,077 filed Apr. 21, 2016, which is incorporated herein by reference in its entirety, which claims the benefit of U.S. Provisional Application No. 62/151,287 filed on Apr. 22, 2015, which is incorporated herein by reference in its entirety.

BACKGROUND

This section is intended to introduce the reader to aspects of art that may be related to various aspects of the present disclosure described herein, which are described and/or claimed below. This discussion is believed to be helpful in providing the reader with background information to facilitate a better understanding of the various aspects of the present disclosure described herein. Accordingly, it should be understood that these statements are to be read in this light, and not as admissions of prior art.

Generally, babies, newborns, and infants frequently require that they be patted or stroked to assist them to relax and fall asleep. Further, such patting is also helpful in treating and alleviating the infant's irritability, fussing, crying, and often sustained screaming. Providing this constant patting is sometimes difficult for busy parents. Their hands frequently fatigue from patting the child, especially while holding the child. Also, when the child is in its crib, it is difficult to pat the child without removing him or her from the crib.

Hence, what is needed is an infant garment that can provide certain vibrations, in an evenly distributed manner, that can mimic patting and massaging of the infant, thereby providing a calming effect to the infant and promote relaxation and sleep and further prevent irritability, fussing, crying, and screaming. In addition, it is desirable for the infant garment to have a child-proof and easily accessible area by an adult for a vibration component of the infant garment, such that the vibration component can be serviceable, replaced, maintained, and/or controlled wirelessly.

BRIEF SUMMARY

In one aspect of the present disclosure described herein, an infant garment is disclosed that can provide certain vibrations, in an evenly distributed manner, that can mimic patting and massaging of the infant, thereby providing a calming effect to the infant and promote relaxation and sleep and further prevent irritability, fussing, crying, and screaming. In addition, the infant garment includes a child-proof and easily accessible pouch area by an adult, wherein the pouch area encloses an electronic vibrating component of the infant garment, such that the vibrating component can be serviced, replaced, maintained, and/or controlled wirelessly, among other advantages.

In another aspect of the disclosure described herein, an infant garment is disclosed having a first compartment disposed in a middle region of the garment, wherein the compartment can also include a first flap and a second flap, wherein the first flap at least partially overlaps the second flap. In addition, the infant garment may also include a second compartment disposed within the first compartment, wherein the second compartment is elastic. Further, the infant garment may also include an vibrating electronic device disposed within the elastic second compartment and secured therein. Here, the second flap at least partially forms a pocket, and wherein the elastic second compartment and vibrating electronic device are disposed within the pocket. In addition, the infant garment can further include a padded layer within the compartment and secured to the second compartment. Here, the padded layer can be disposed below the second compartment such that is in direct contact with either the second compartment or the vibrating electronic device. In addition, the infant garment may include a cover disposed over the second compartment and the padded layer. Here, the cover can include a first end fixed to the first compartment, second compartment, or padded layer. The cover can further include an opposing second end that is free or unsecured. The cover may also include an opposing second end that is coupled to the first compartment, second compartment, or padded layer via a fastener. In addition, a fastener can be configured to secure the first flap and second flap. Here, the electronic vibrating device can be a tubular or cylindrical configuration, and further include a vibrating motor operable at various intensities. Here, the operation of the electronic vibrating device can be controlled via a wireless controller.

The above summary is not intended to describe each and every disclosed embodiment or every implementation of the disclosure. The Description that follows more particularly exemplifies the various illustrative embodiments.

BRIEF DESCRIPTION OF THE DRAWINGS

The following description should be read with reference to the drawings, in which like elements in different drawings are numbered in like fashion. The drawings, which are not necessarily to scale, depict selected embodiments and are not intended to limit the scope of the disclosure. The disclosure may be more completely understood in consideration of the following detailed description of various embodiments in connection with the accompanying drawings, in which.

DETAILED DESCRIPTION

In the Brief Summary of the present disclosure above and in the Detailed Description of the disclosure described herein, and the claims below, and in the accompanying drawings, reference is made to particular features (including method steps) of the disclosure described herein. It is to be understood that the disclosure of the disclosure described herein in this specification includes all possible combinations of such particular features. For example, where a particular feature is disclosed in the context of a particular aspect or embodiment of the disclosure described herein, or a particular claim, that feature can also be used, to the extent possible, in combination with and/or in the context of other particular aspects and embodiments of the disclosure described herein, and in the disclosure described herein generally.

The embodiments set forth below represent the necessary information to enable those skilled in the art to practice the disclosure described herein and illustrate the best mode of practicing the disclosure described herein. In addition, the disclosure described herein does not require that all the advantageous features and all the advantages need to be incorporated into every embodiment of the disclosure described herein.

Phrases and terms similar "network" may include one or more data links that enable the transport of electronic data between computer systems and/or modules. When information is transferred or provided over a network or another communications connection (either hardwired, wireless, or a combination of hardwired or wireless) to a computer, the computer uses that connection as a computer-readable medium. Thus, by way of example, and not limitation, computer-readable media can also comprise a network or data links which can be used to carry or store desired program code means in the form of computer-executable instructions or data structures and which can be accessed by a general purpose or special purpose computer.

Phrases and terms similar to "software", "application", and "firmware" may include any non-transitory computer readable medium storing thereon a program or algorithm, which when executed by a computer, causes the computer to perform a method, process, or function.

Figure 1A:
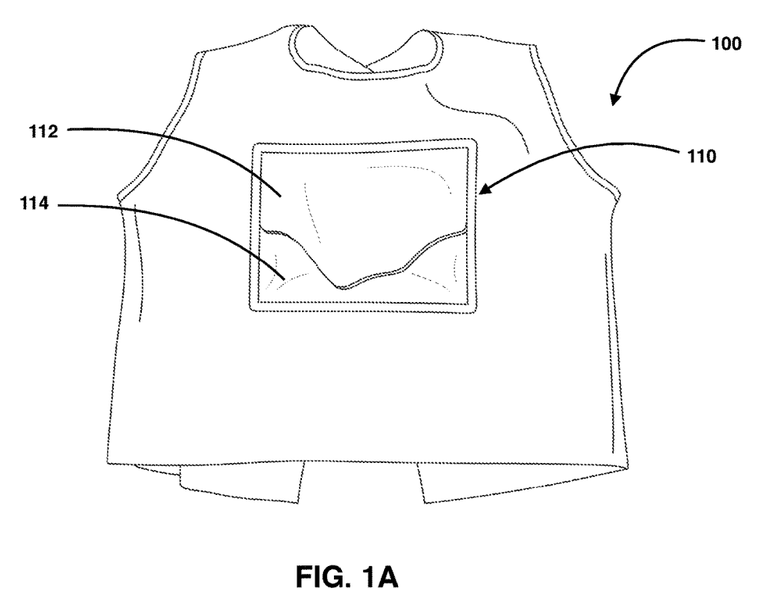
FIG. 1A illustrates a front view for one non-limiting embodiment of the vibrating infant garment of the disclosure described herein.
Figure 1B:
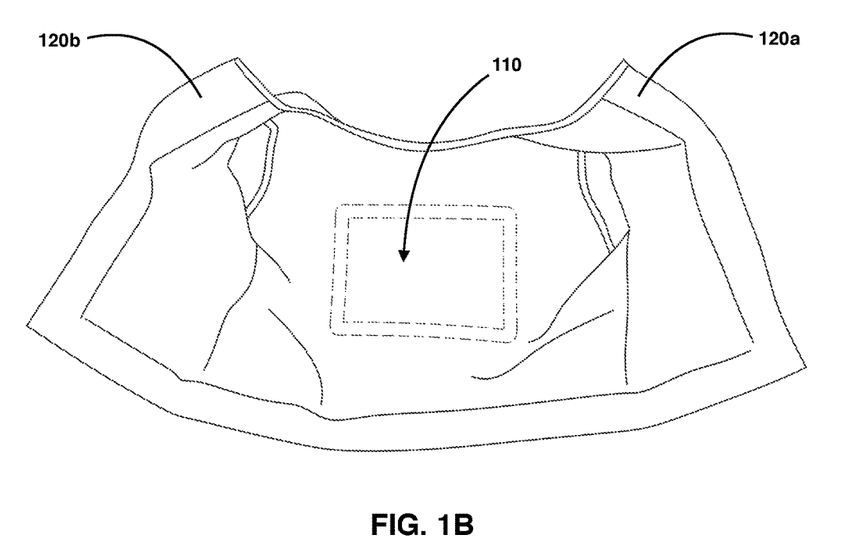
FIG. 1B illustrates an expanded rear and interior view of the vibrating infant garment of the disclosure described herein.
Figure 4A:
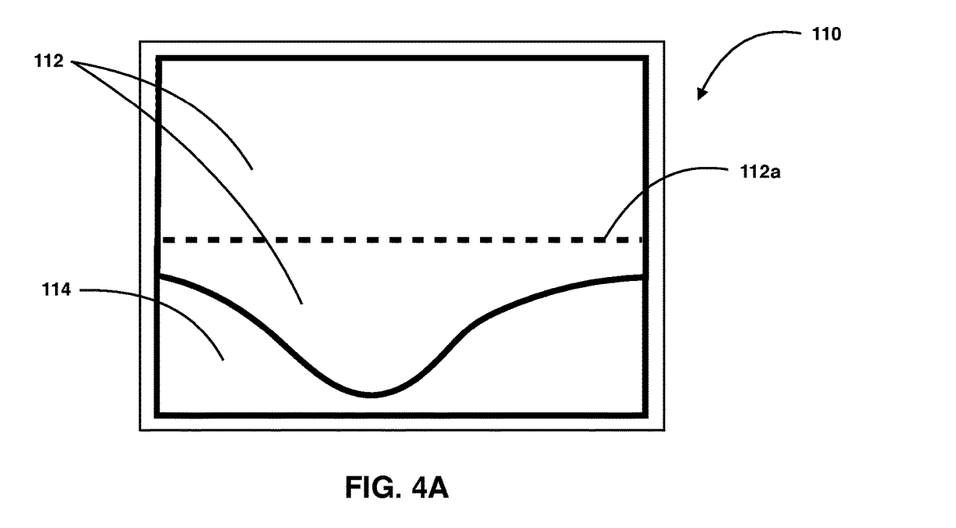
FIG. 4A illustrates another top view of the compartment of the vibrating infant garment of the disclosure described herein.
Figure 4B:
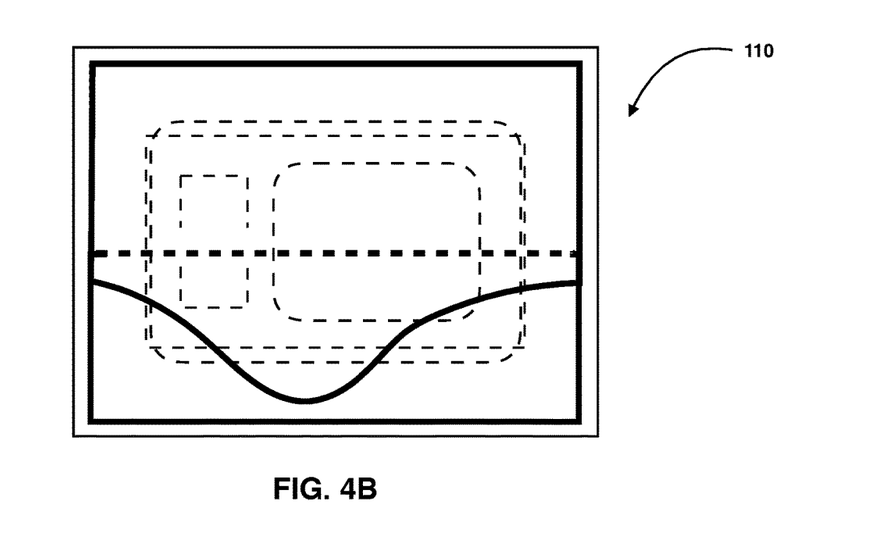
FIG. 4B illustrates another top view of the compartment of the vibrating infant garment, further partially illustrating components within its interior, of the disclosure described herein.

FIGS. 1A-1B illustrates one embodiment for an infant garment of the disclosure described herein. More specifically, garment 100 is shown having a pocket, pouch, enclosure, storage, chamber, or compartment 110 having a top flap 112 piece and a lower bottom flap 114 piece, wherein flaps 112 and 114 overlap with respect to each other, as also shown in FIGS. 4A-4B, to enclose the interior of compartment 110. It is contemplated within the scope of the disclosure described herein that compartment 110 may have any type of size, configuration, or dimension, and may further include any type of artwork, stitching, embroidery, patches, or indicia thereon. Here compartment 110 may be manufactured as part of garment 100, or in the alternative, compartment 110 may be an independent component that is later secured, fastened, and/or stitched onto garment 100. FIG. 1B illustrates an interior view of garment 100, more particularly illustrating the stitching pattern of compartment 110 as viewed from the interior, and the middle area approximate location of compartment 110.

In addition, garment 100 may include flaps 120a and 120b that can be secured to each other via any type of fastener. Here, the configuration garment 100, with its large open sleeveless cut-outs and simple detachable flaps 120a/120b, allow it to be easily placed onto or removed from an infant child or baby. For example, garment 100 may also be worn by the infant child over his or her existing clothing. However, it is contemplated within the scope of the disclosure that garment 100 may also be configured in any shape or configuration, such as a one-piece body suit (i.e. "onesie"), t-shirt, pajamas, sleeved shirt, blanket, or any other wearable or wrap-around apparel. Generally, the infant garment is designed so that it can be placed on to the infant while the infant is lying on his or her backside. However, garment 100 may also be worn backwards by the infant such that compartment 110 rests on the back of the infant. Alternatively, the compartment 110 may also be secured to the backside of any other type of garment.

Figure 2A:
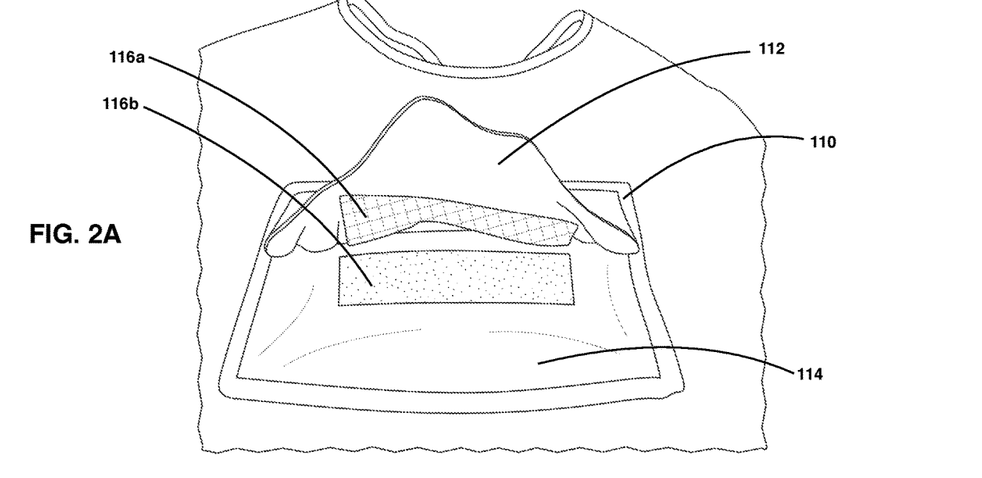
FIG. 2A illustrates a close-up top perspective view of a compartment of the vibrating infant garment of the disclosure described herein.
Figure 2B:
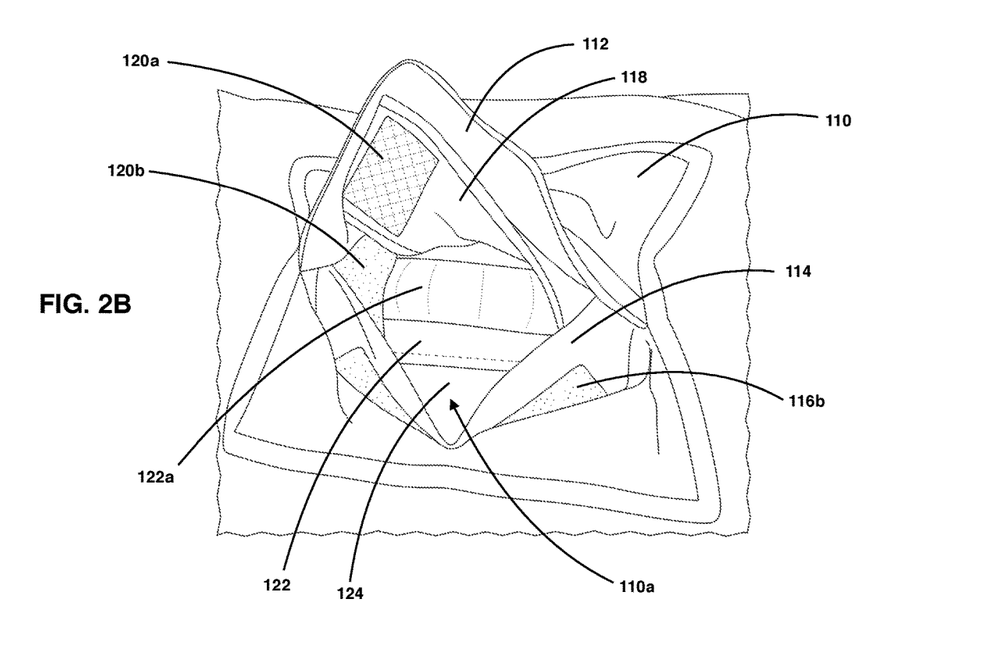
FIG. 2B illustrates another close-up top perspective view of an interior of the compartment of the vibrating infant garment of the disclosure described herein.

FIGS. 2A-2B illustrate close-up views of the enclosure 110, having the flap 112 with one or more fastening members 114 for securely closing the opening 110a of enclosure 110. More specifically, the interior area of enclosure 110 may be accessed through opening 110a. Here, it is contemplated within the scope of the disclosure described herein that any type of fastening member may also be used, including but not limited to hook and loop (Velcro®), zipper, buttons, snaps, adhesive, or stitching.

Still referring to FIGS. 2A-2B and also FIGS. 4A-6, compartment 110 is shown situated in a position and location on the garment such that it sits on top the top chest area of an infant when garment 100 is worn. In repeated trial and error experiments, this configuration was shown to provide the most effective area in calming or soothing an agitated infant. Here, top flap 112 and bottom flap 114 can be secured to each other via a hook and loop fastener 116a secured to flap 112 and another hook and loop fastener 116b secured to bottom flap 114.

Figure 5A:
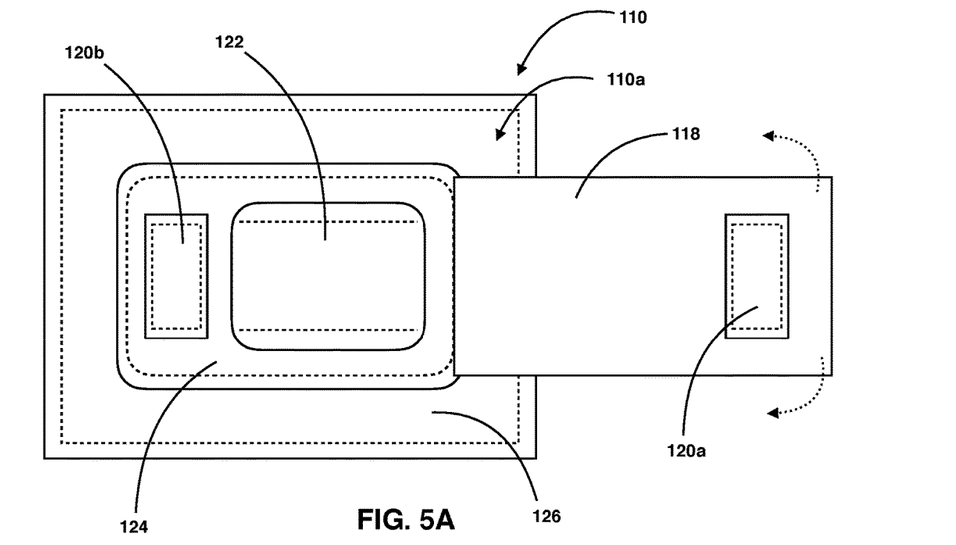
FIGS. 5A-5B illustrate top views of an interior region of the compartment of the vibrating infant garment, further illustrating components within its interior, of the disclosure described herein.
Figure 5B:
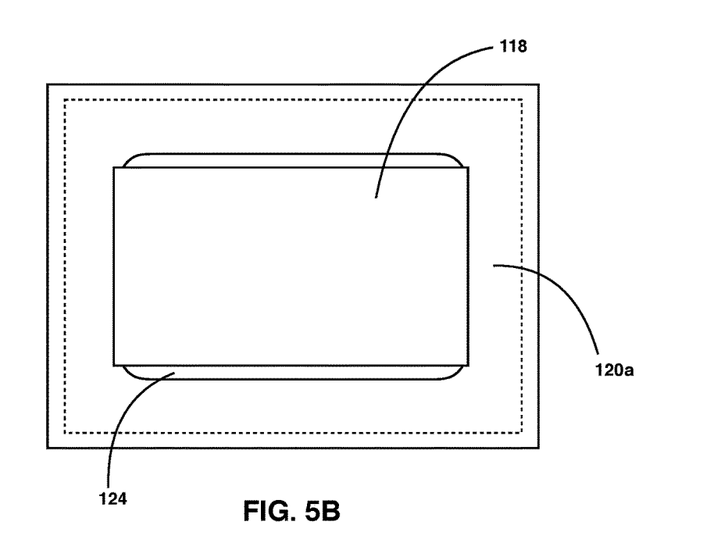
Figure 6:
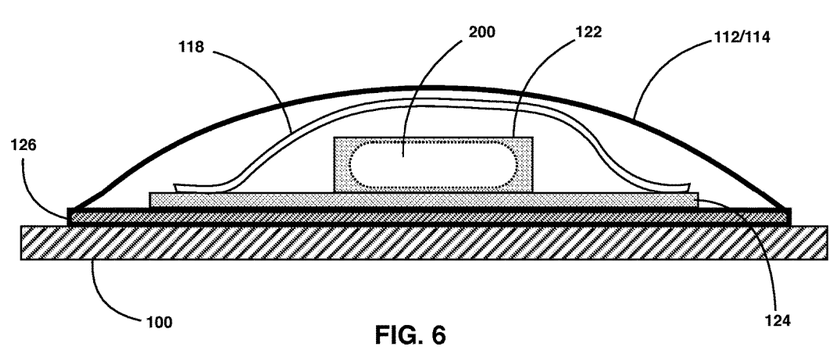
FIG. 6 illustrates a partial cross-sectional view of the compartment and its interior components of the disclosure described herein.

Moreover, interior region 110a of compartment 110 can further include a main underlayment layer 126, as shown in FIG. 5A and FIG. 6, that is secured to main garment 100. In addition, the interior region 110a of compartment 110 can further include a vibration dispersion padding layer 124 that is further secured to layer 126 or garment 100. Here, padding layer 124 is configured such that it can evenly distribute vibrations and oscillations from a vibration component or device 200 across the chest are of the infant in a uniform manner. Further, padding layer 124 may also provide a dampening effect to the vibrations of device 200 and may be flexible, rigid, or non-rigid. Here, padding layer 124 can be made of any material, including but not limited to cotton, wool, polyester, rubber, metal, polyurethane, or any other suitable material.

Figure 3A:
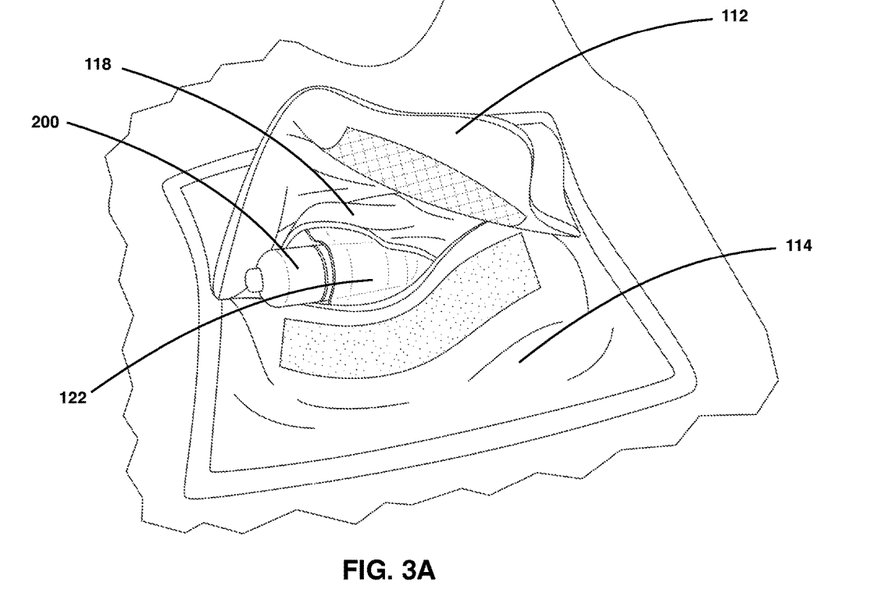
FIG. 3A illustrates another close-up top perspective view of an interior of the compartment further illustrating a vibrating component of the vibrating infant garment of the disclosure described herein.

Still referring to FIGS. 2A-2B and FIGS. 4A-6, the interior of compartment 110 can further include an elastic and expandable sub-compartment layer 122 having a slightly arched region 122a and an opening therein to securely hold and enclose vibration device 200, as also shown in FIG. 3A. Here, sub-compartment 122 is further secured and fastened to layer 124 via top and bottom stitching, such that it distributes the vibrations of device 200 to layer 124. In addition, since vibration device 200 is at least partially wrapped tightly around and within sub-compartment 122, it further helps provide a child-proof barrier to prevent an infant from attempting to remove device 200.

Here, sub-compartment 122 includes a tubular compartment therein for housing device 200 in which sub-compartment 122 is elastic and stretchable to provide a secure fit for device 200. In addition, the interior of compartment 110 may further include cover layer 118. Here, cover layer 118 is secured or fixed to one end of layer 124 and can pivot about an axis. Moreover, cover layer 118 may be either be cloth, fabric, wool, polyester, cotton, padding, or rubber. Here, cover layer 118 may further have a fastener 120a to engage with a faster 120b secured to layer 124, such that another opposing free end of cover 118 can be secured to layer 124. Here, fasteners 120a and 120b may be hook and loop fasteners or any other suitable fastener. Cover layer 118 is generally configured such that it adds another layer of child-proof protection over sub-compartment 122 and vibration device 200. Here, it is contemplated within the scope of the disclosure described herein that any type of fastener may be used for fasteners 116a, 116b, 120a, or 120b, including but not limited to hook and loop (Velcro®), zipper, buttons, snaps, adhesive, or stitching, rings, straps, loop straps, hooks, or the like.

Figure 3B:
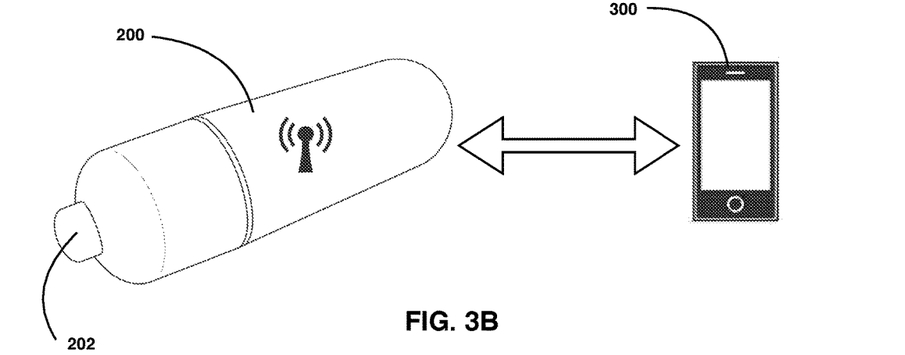
FIG. 3B illustrates a perspective view and diagram of a vibrating component communicating bi-directionally with a wireless device.

Referring now to FIG. 3B, vibration device 200 may be generally cylindrical in shape and having circuitry, one or batteries, motor, software, and hardware disposed therein. In addition vibration device 200 may be waterproof and operable via push button 202, which may turn the device on/off and control intensity of the vibrations. Further, vibration device 200 may have wireless communication capability, such as via Bluetooth® or Wi-Fi that can communication bi-directionally over a network with a remote computing device or controller 300. Here, controller or device 300 may allow an adult user to control the operation of vibration device 200, such as on/off and vibration intensity. For example, remote computing device may be a mobile phone device having software or applications thereon to facilitate control of vibration device 200, such as via intensity, frequency, and/or scheduling. In addition, the vibrations may be either continuous, pulsed, or interchange between a pulsed and continuous pattern. In addition, device 200 may also include speakers and audio playback hardware and software to emit various sounds, audio, voices, or music, which may be pre-programmed. Here, the vibrator motor may operate in cycles that can range from 500 RPM up to 12000 RPM.

In addition, the vibrating device may further include various types of voltage regulation and/or feedback loops to monitor and control vibration intensity. For example, the vibrator may include an "intelligent" system or software that can learn various patterns or operational intensity. Specifically, the vibrating device may include one or more sound capturing or microphones to detect the sounds of infant crying and operate the motor of the vibration device to at a pre-set RPM or vibration intensity until the device detects that the infant is no longer crying. Alternatively, the vibrating device may also be able to detect the heart rate of the infant as well and modify vibration intensity of the motor in response there to.

Having thus described the several embodiments of the present disclosure described herein, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes can be made with respect to various elements described herein without exceeding the scope of the invention. Although the present disclosure described herein has been described in considerable detail with reference to certain preferred versions or embodiments thereof, other versions and embodiments are possible. Therefore, the spirit and scope of the appended claims should not be limited to the description of the embodiments contained herein.

What is claimed is:

1. An infant garment, comprising:
    a first compartment disposed in a middle region of the garment, the compartment further comprising a first flap and a second flap, wherein the first flap at least partially overlaps the second flap;
    a second compartment disposed within the first compartment, wherein the second compartment is elastic;
    a padded layer within the first compartment and secured to the second compartment; and
    a vibrating electronic device disposed within the elastic second compartment and secured therein.

2. The infant garment of claim 1, wherein the second flap at least partially forms a pocket, and wherein the elastic second compartment and vibrating electronic device are disposed within the pocket.

3. The infant garment of claim 1, wherein the operation of the electronic vibrating device is controlled via a wireless controller.

4. The infant garment of claim 1, wherein the padded layer is disposed underneath the second compartment wherein it is in direct contact with either the second compartment or the vibrating electronic device.

5. The infant garment of claim 1, further comprising a cover disposed over the second compartment and the padded layer.

6. The infant garment of claim 5, wherein the cover further comprises a first end coupled to the first compartment, second compartment, or the padded layer.

7. The infant garment of claim 6, wherein the cover further comprises an opposing second end that is free or unsecured.

8. The infant garment of claim 6, wherein the cover further comprises an opposing second end that is coupled to the first compartment, second compartment, or padded layer via a fastener.

9. The infant garment of claim 1, further comprising a fastener configured to secure the first flap and second flap.

10. The infant garment of claim 1, wherein the electronic vibrating device is comprised of a tubular or cylindrical configuration, and further comprises a vibrating motor operable at various intensities.

11. The infant garment of claim 1, wherein the operation of the electronic vibrating device is controlled via a wireless controller.

12. The infant garment of claim 1, wherein the electronic vibrating device is comprised of a tubular or cylindrical configuration, and further comprises a vibrating motor operable at various intensities.

13. An infant garment, comprising:
    a first pocket disposed in a middle region of the garment;
    a second pocket disposed within the first pocket, wherein the second pocket is elastic;
    a padded layer within the first pocket and secured to the second pocket; and
    a vibrating electronic device at least partially disposed within the elastic second pocket and secured therein.

14. The infant garment of claim 13, further comprising a cover disposed over the second pocket and the padded layer.

15. The infant garment of claim 14, wherein the cover further comprises a first end secured to the first pocket, second pocket, or the padded layer.

16. The infant garment of claim 15, wherein the cover further comprises an opposing second end that is free or unsecured.

17. The infant garment of claim 15, wherein the cover further comprises an opposing second end that is coupled to the first pocket, second pocket, or the padded layer via a fastener.

18. The infant garment of claim 13, wherein the padded layer is disposed underneath the second pocket wherein it is in direct contact with either the second pocket or the vibrating electronic device.

* * * * *